US009375186B2

(12) United States Patent
Sola i Caros et al.

(10) Patent No.: US 9,375,186 B2
(45) Date of Patent: Jun. 28, 2016

(54) METHOD AND APPARATUS FOR ESTIMATING A PULSE ARRIVAL TIME VALUE (71) Applicant: CSEM SA, Neuchâtel (CH)

(72) Inventors: Josep Sola i Caros, Neuchâtel (CH); Josef X. Brunner, Chur (CH)

(73) Assignee: CSEM SA, Neuchatel (CH)

( * ) Notice: Subject to any disclaimer, the term of this patent is extended or adjusted under 35 U.S.C. 154(b) by 680 days.

(21) Appl. No.: 13/737,169

(22) Filed: Jan. 9, 2013

(65) Prior Publication Data

US 2013/0218031 A1  Aug. 22, 2013

Related U.S. Application Data (63) Continuation of application No. PCT/EP2011/061757, filed on Jul. 11, 2011.

(60) Provisional application No. 61/344,399, filed on Jul. 13, 2010.

(51) Int. Cl.
A61B 5/02 (2006.01)
A61B 5/021 (2006.01)
A61B 5/00 (2006.01)
A61B 5/0285 (2006.01)
A61B 5/053 (2006.01)

(52) U.S. Cl.
CPC .............. A61B 5/7278 (2013.01); A61B 5/021 (2013.01); A61B 5/0285 (2013.01); A61B 5/02125 (2013.01); A61B 5/0536 (2013.01)

(58) Field of Classification Search
USPC ........................................................ 600/485
See application file for complete search history.

(56) References Cited

U.S. PATENT DOCUMENTS 5,651,955 A    7/1997 Klaveness
2003/0229451 A1*  12/2003 Hamilton ........... G01N 30/8655
                                                      702/19

OTHER PUBLICATIONS

"Localisation of cardiac related impedance changes in the thorax", B. N. Eyüboglu et al., Clin. Phys. Phyiol. Meas. 1987, vol. 8.
"Pulmonary perfusion and ventricular ejection imaging by frequency domain filtering of EIT images", M. Zadehkoochak et al., Clin. Phys. Physiol. Meas., 1992, vol. 13.

(Continued)

Primary Examiner — Michael Kahelin
Assistant Examiner — Mitchell E Alter
(74) Attorney, Agent, or Firm — Pearne & Gordon LLP (57) ABSTRACT Method and apparatus for estimating an arrival time (PAT) value of a subject in an automatic and unsupervised fashion from a sequence of electrical impedance tomography (EIT) images. The method comprises: providing an EIT imaging device adapted to record impedance signal distribution within a measurement region of the subject; measuring a sequence of temporally discrete EIT images during a predetermined measuring time period in the measurement region using the EIT imaging device, each EIT image comprising one or a plurality of EIT pixel subsets, each of said one or a plurality of EIT pixel subset representing an impedance value; generating one or a plurality of time series, each of said one or a plurality of time series representing a variation of the impedance value of the sequence of EIT images; and estimating the PAT value from each of said one or a plurality of time series.

20 Claims, 6 Drawing Sheets

(56) References Cited

OTHER PUBLICATIONS

"Noninvasive Assessment of Right Ventriclar Diastolic Function by Electrical Impedance Tomography", A. V. Noordegraaf, et al., Chest, 1997, vol. 111.

"Determination of stroke volume by means of electrical impedance tomography", A. V. Noordegraaf, et al., Physiol. Meas., 2000, vol. 21.

"Dynamic separation of pulmonary and cardiac changes in electrical impedance tomography", J. M. Deibele, et al., Physiol. Meas., 2008, vol. 29.

"Regional Lung Perfusion as Determined by Electrical Impedance Tomography in Comparison With Electron Beam CT Imaging", Inez Frerichs et al., IEEE Transactions on Medical Imaging, vol. 21, No. 6, Jun. 2002.

"Parametric Estimation of Pulse Arrival Time: A Robust Approach to Pulse Wave Velocity", Josep Sola, Phsysiological Measurement, 2009, vol. 30.

International Search Report dated Sep. 29, 2011 for application PCT/EP2011/061757.

\* cited by examiner

Fig. 1 (State of art)

Fig. 2 (State of art)

Fig. 3 (State of art)

METHOD AND APPARATUS FOR ESTIMATING A PULSE ARRIVAL TIME VALUE

FIELD

The present disclosure relates to a method and apparatus for estimating a pulse arrival time (PAT) value of a subject in an automatic and unsupervised fashion.

DESCRIPTION OF RELATED ART

The demand for devices to assess and monitor human cardiovascular function non-invasively, non-obtrusively and in real time in both, clinical and ambulatory conditions is continuously increasing: while reducing the need for long hospitalization periods, non-invasive monitors also reduce healthcare costs and improve patient comfort. In recent years, electrocardiograms, blood pressure monitors and pulse oximeters have been successfully released into the market paving the way towards the monitoring of cardiac and vascular parameters in hospitals and in out-patients alike. Unfortunately, these parameters still provide an incomplete picture of a patient's health status and do not fully fulfill clinical demand.

Recently, Electrical Impedance Tomography (EIT) has been used in the monitoring cyclic movement of blood within the chest. From an electrical perspective, the thoracic cavity can be viewed as a complex distribution of impedance volumes. While the lungs (filled with air cavities) form high impedance volumes, the heart (filled with blood) forms a compact and blood vessels branching trees of low impedance volumes. As discussed in Reference 1: "Electrical Impedance Tomography: Methods, History and Applications", David S. Holder. Institute of Physics, Series on Medical Physics and Biomedical Engineering, ISBN 0 7503 0952 0, 2005, EIT creates tomographic reconstructions of the distribution of impedances within the thoracic cavity.

Figure 1:
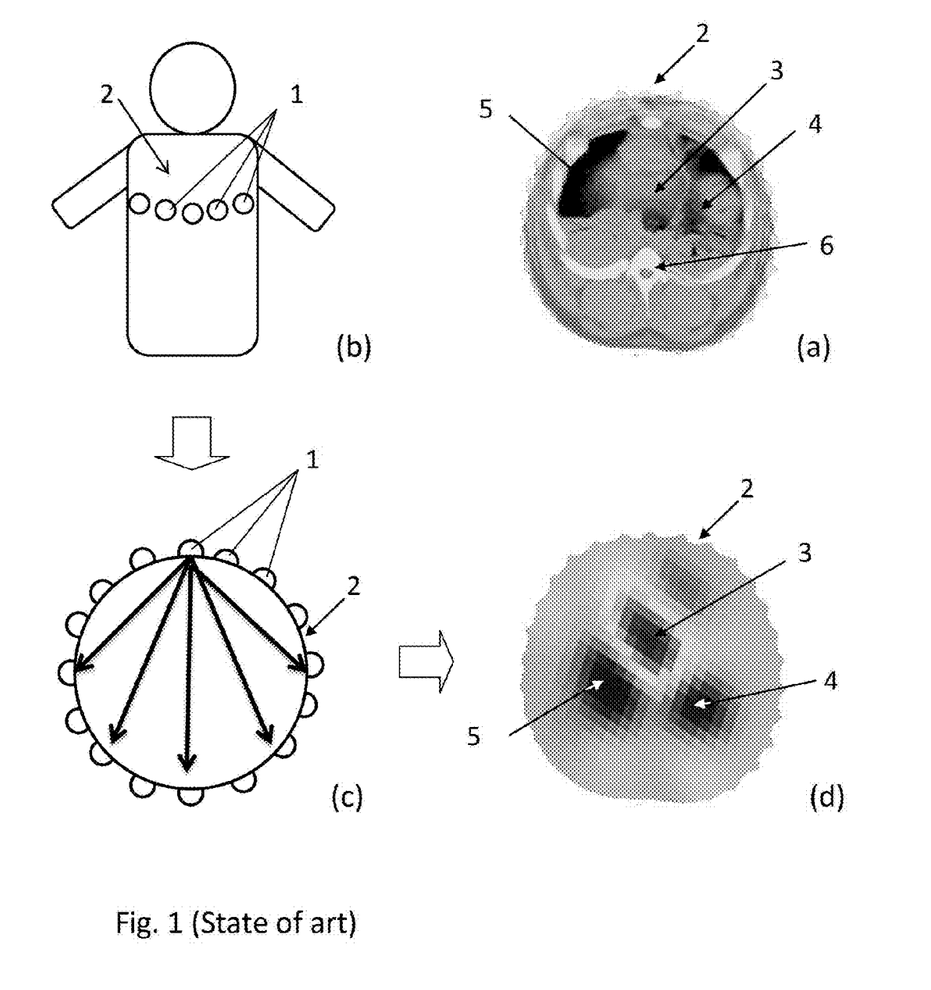

As input signals, EIT requires a set of impedance measurements performed around the chest (see FIG. 1 (b)). Basic a-priori knowledge about chest anatomy allows then to estimate the most likely impedance distribution given the set of measurements, and to determine specific regions of interest, such as the heart and the lungs. FIGS. 1 (b) to 1 (d) represent an estimation of blood movement within the chest using EIT. After placing several electrodes 1 around the chest 2 (FIG. 1 (b)), impedance measurements are performed for each electrode pair 1 where the arrows represent typical electrical propagation paths (FIG. 1 (c)). Tomographic images are then constructed (FIG. 1 (d)) with the dark areas representing the heart 3, the right lung 4 and left lung 5. By analyzing a series of images obtained during a complete cardiac cycle, one obtains information on the cyclic movement of blood within the chest. A computerized tomography (CT)-scan of pig chest 2 is provided as anatomical reference (FIG. 1 (a)). In the CT-scan of FIG. 1 (a) the heart 3, right lung 4, left lung 5, and back bone 6 are visible. With the help of EIT technology, fast in-vivo images of the thoracic cavity (up to 50 images/second) can be obtained simply requiring the placement of several electrodes around the thorax (e.g., in a simple chest belt or in more sophisticated anatomy-adjusted configurations).

Figure 2:
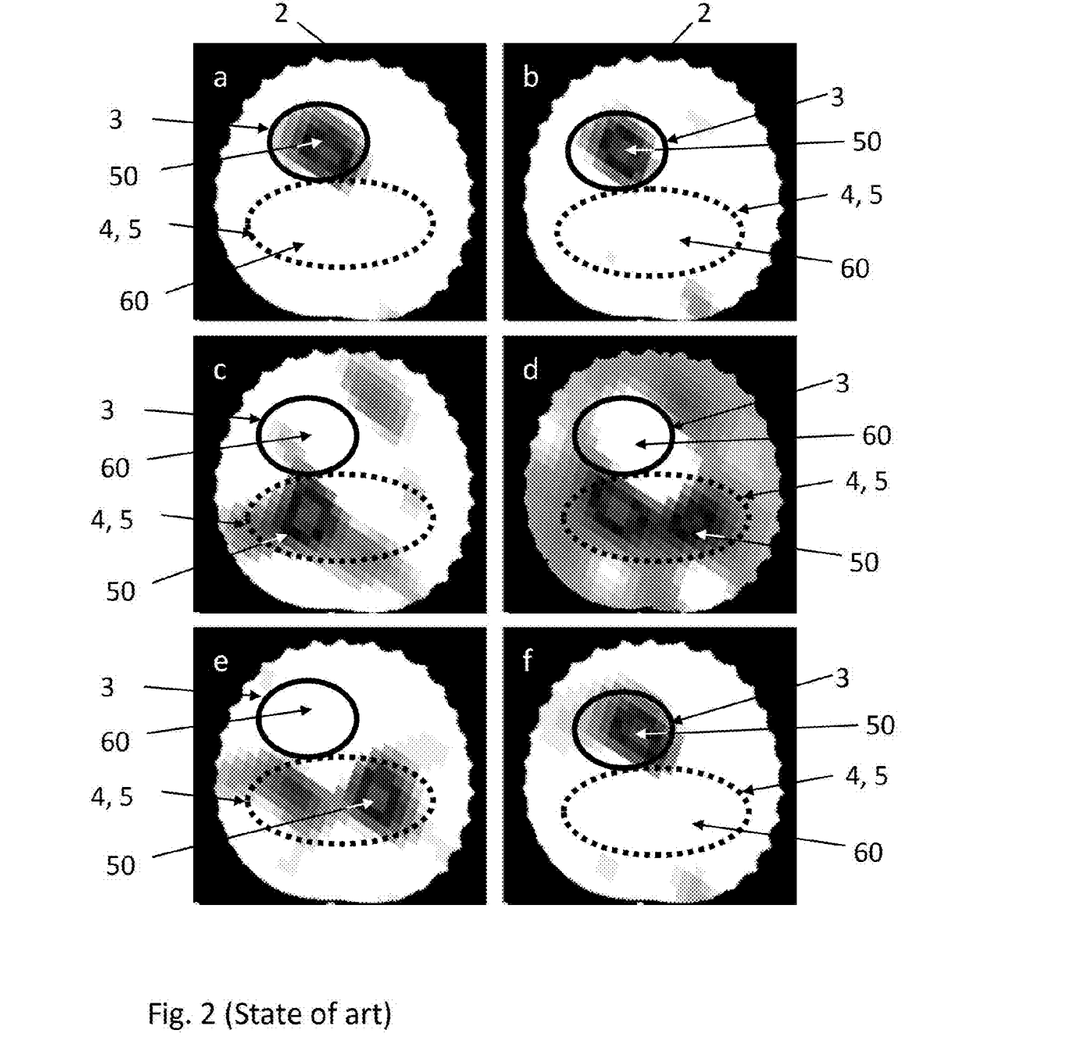

During each cardiac cycle, vascularized structures within the thorax receive bursts of highly electrically conductive blood, which decreases their local impedance provided these vessels expand locally. Hence, when comparing a sequence of EIT images acquired during a complete cardiac cycle, one is able to visualize the pulsation of these structures caused by the changing pressures within them. These pulsating structures are either the heart as such or major vessels running either within the EIT field of observation (pulmonary artery) or through it (aorta). An example of EIT-based visualization of blood pulsation from the heart 3 to the lungs 4, 5 of an anesthetized pig is illustrated in FIGS. 2 (a) to (f). FIGS. 2 (a) to (f) show tracking of blood as it moves through the heart 3 and lungs 4, 5 during a cardiac cycle. EIT images show the local filling of blood in the areas indicated by the numeral 50 and emptying in the areas indicated by the numeral 60. The heart region 3 has been delineated by the solid black line and the lung regions 4, 5 by the dashed black lines. More particularly, in FIGS. 2 (a) and (b) one observes the filling of the heart 3. In FIG. 2 (c) the heart empties while the right lung 4 (here on the left hand side) is starting to be perfused. In FIGS. 2 (d) and (e) both lungs 4, 5 are perfused. Finally, in FIG. 2 (f) the cardiac cycle starts again.

The exploitation of cardiogenic pulsatility information (so called perfusion) represented in sequences of EIT images has already been performed in the past. In "Localisation of cardiac related impedance changes in the thorax", B. N. Eyüboglu et al., Clin. Phys. Phyiol. Meas. 1987, Vol 8, it was first proposed to analyze the changes in impedance distribution within the thorax during a full cardiac cycle. By comparing the changes in impedance distribution across the different EIT images, they described the filling and emptying of the ventricles and the perfusion of the lungs.

Reference 2: "Pulmonary perfusion and ventricular ejection imaging by frequency domain filtering of EIT images", M. Zadehkoochak et al., Clin. Phys. Physiol. Meas., 1992, Vol 13, proposes a method to decompose a sequence of EIT images into its pulmonary (ventilation) and its cardiogenic (perfusion) components, based on a frequency-domain analysis.

Reference 3: "Noninvasive Assessment of Right Ventriclar Diastolic Function by Electrical Impedance Tomography", A. V. Noordegraaf, et al., Chest, 1997, Vol 111, proposes a method to assess ventricular diastolic function by first identifying the heart region within a sequence of EIT images; and then by monitoring the changes of impedance at the identified region occurring during the different phases of the cardiac cycle. The heart chambers are identified by visualizing the changes of impedance distribution in an ECG-gated EIT image sequence.

Reference 4: "Determination of stroke volume by means of electrical impedance tomography", A. V. Noordegraaf, et al., Physiol. Meas., 2000, Vol 21, proposes to measure Stroke Volume changes via a similar method as in 1997. Here, the identification of the heart region was done by averaging EIT pixel data through a full cardiac cycle. By setting a threshold on the amount of impedance change, those pixels exceeding the threshold were assigned to the heart region of interest (ROI). An energy feature for each pixel was thus defined.

In Reference 5: "Dynamic separation of pulmonary and cardiac changes in electrical impedance tomography", J. M. Deibele, et al., Physiol. Meas., 2008, Vol. 29, it is also proposed a method to decompose a sequence of EIT images into its pulmonary (ventilation) and its cardiogenic (perfusion) component, based on a Principal Component Analysis.

Reference 6: "Determination of stroke volume by means of electrical impedance tomography", A. V. Noordegraaf, et al., Physiol. Meas., 2000, Vol. 21, discloses a method to separate ventilation-related from perfusion-related regions within sequences of EIT images by analyzing the energy that pixels depict within different frequency bands.

Two main limitations of the methods described above are to be underlined. On the one hand, the state-of-the-art methods provide only qualitative information on organ perfusion.

They are able to provide: either the position of a given organ within the EIT image, or the relative change of impedance values for a certain region throughout the cardiac cycle. None of these parameters being directly related to a physiological measurement, these methods provide values expressed in arbitrary units. Hence, one is not able to provide absolute measurements such as mL of blood volume, or mmHg of blood pressure without additional calibration means. On the other hand, impedance changes occurring at the lung regions through the respiratory cycle, and impedance changes occurring at the heart and lung regions through the cardiac cycle mask many other impedance changes occurring within the chest throughout the cardiac cycle. Hence, the processing methods as described in the state of the art fail at identifying smaller perfused regions such as the aorta or the pulmonary arteries.

SUMMARY

The present disclosure concerns a method to process a sequence of Electrical Impedance Tomography (EIT) images comprising the steps of: estimating the Pulse Arrival Time (PAT) of at least one signal indicative of a pressure pulse within the EIT field of observation; and creating an image, representative of the sequence of EIT images, for which pixel values correspond to the Pulse Arrival Time (PAT) values.

Further disclosed is a method for estimating an arrival time value of arterial pressure pulses (PAT value) of a subject from a sequence of electrical impedance tomography (EIT) images, comprising: providing an EIT imaging device adapted to record impedance signal distribution (EIT image) within a measurement region of the subject; measuring a sequence of temporally discrete EIT images during a predetermined measuring time period in the measurement region using the EIT imaging device, each EIT image comprising one or a plurality of EIT pixel subsets, each of said one or a plurality of EIT pixel subset representing an impedance value; generating one or a plurality of time series, each of said one or a plurality of time series representing a variation of the impedance value of the sequence of EIT images; and estimating the PAT value from each of said one or a plurality of time series.

In an embodiment, the estimation of PAT values is performed in an automatic and unsupervised way.

In another embodiment, the estimation of PAT values is performed based on the analysis of time series describing changes of impedance for each pixel in the sequence of EIT images.

In yet another embodiment, the estimation of PAT values is performed based on the analysis of time series describing changes of impedance of groups of pixels in the sequence of EIT images.

In yet another embodiment, each time series is ensemble averaged via an ECG-gated ensemble averaging procedure, providing a single ensemble-averaged impedance pulse waveform.

In yet another embodiment, each time series is ensemble averaged via an EIT-gated ensemble averaging procedure, providing a single ensemble-averaged impedance pulse waveform.

In yet another embodiment, the EIT-gated ensemble averaging procedure is gated with the onset of left- and/or right ventricular contraction, as detected from the analysis of the sequence of EIT images.

In yet another embodiment, the estimation of PAT values is performed on the time series of impedance changes.

In yet another embodiment, the estimation of PAT values is performed on the ensemble-averaged impedance pulse waveform.

In yet another embodiment, the estimation of PAT values is performed by applying parametric estimation techniques.

In yet another embodiment, the estimation of PAT values is performed by applying single-point-based techniques.

In yet another embodiment, the creation of time-based images implies discarding PAT values according to selection criteria.

In yet another embodiment, the selection criteria is a confidence index obtained during the PAT estimation procedure.

The present disclosure also pertains to an apparatus for estimating the PAT value, comprising: an EIT imaging device comprising a plurality of electrodes to be placed in operative cooperation with the chest of the subject and adapted to measure the sequence of temporally discrete EIT images; an input module for inputting the sequence of EIT images; a processing unit for performing the step of estimating the PAT value; and an output module for outputting the PAT value.

The method disclosed herein can provide absolute quantities expressed in measurement units used in current clinical practice, and detecting and monitoring organs and anatomical structures represented by small regions of interest such as the aorta or the pulmonary arteries is desired. Moreover, the method can provide absolute quantities in an automatic and unsupervised way without having to rely on a-priori information about the thoracic structure to be analyzed.

BRIEF DESCRIPTION OF THE DRAWINGS

The invention will be better understood with the aid of the description of an embodiment given by way of example and illustrated by the figures, in which:

FIGS. 1 (a) to (d) represent an estimation of blood movement within the chest using electrical impedance tomography (EIT);

FIGS. 2 (a) to (f) show tracking of blood as it moves through the heart and lungs of an anesthetized pig during a cardiac cycle;

FIGS. 4 (a) to (e) illustrate the different steps of estimating the PAT value and generating a time-based PAT image, according to an embodiment;

DETAILED DESCRIPTION OF POSSIBLE EMBODIMENTS

Each time a pressure pulse reaches a segment of the arterial tree (either at the systemic or pulmonary circulation), it induces a temporary increase of the volume of conductive blood, locally decreasing the electrical impedance, and generating thus a so-called impedance pulse. Hence, an impedance pulse as measured by Electrical Impedance Tomography (EIT) is a surrogate of the underlying physiological phenomenon: the pressure pulse. Here, the expression "pressure pulse" corresponds to blood bursts through vascularized structures, or arterial tree, of a human or animal subject during each cardiac cycle, as described above. It also corresponds to the propagation of pressure pulses through the arterial tree.

While the amplitude of pressure pulses is measured in mmHg, the amplitude of impedance pulses is measured in Ohms. The definition of a conversion rule between Ohms and mmHg is not straightforward, and depends on several local arterial biomechanics and bioelectrical characteristics such as local vessel stiffness, local vessel diameter and blood electrical conductivity. This is a main drawback of the state-of-the-art methods to process EIT impedance pulses, since one is not able to provide clinically meaningfully parameters in a straightforward manner.

Although the amplitude information contained within impedance pulses (in Ohms) is difficult to associate with the amplitude information of pressure pulses (in mmHg), the timing information coded in both, i.e., within the impedance pulse waveforms and within the pressure pulse waveforms, is equivalent. In particular, the onset of the pressure pulse at a given anatomical location instantaneously induces the onset of the associated impedance pulse. Hence, the arrival time values of arterial pressure pulses, or Pulse Arrival Time (PAT) values, extracted from impedance pulses correspond to PAT values extracted from pressure pulses, in terms of seconds. The present disclosure thus exploits this correspondence and, rather than extracting amplitude-based information from sequences of EIT images, time-based information is extracted from sequences of EIT images.

In particular, the present disclosure describes the construction of time-based EIT images, the pixels of which depict the arrival time of arterial pressure pulses, measured as impedance pulses, for the associated anatomical regions within an EIT measurement region of the subject. Arrival time values are expressed as the delay, in seconds, from the onset of a ventricular contraction to the arrival of the corresponding pressure pulse at the anatomical region of interest.

A method to construct time-based EIT images comprises the following steps:

initially, a sequence of EIT images is acquired;

from each pixel in the EIT images, a time series representing its changes in impedance values is generated;

for each generated impedance time series, an estimate of the time at which pressure pulses reach the associated anatomical region is obtained, the so-called Pulse Arrival Time (PAT); and a time-based image is constructed, associating to each pixel its estimated PAT value.

Figure 4:
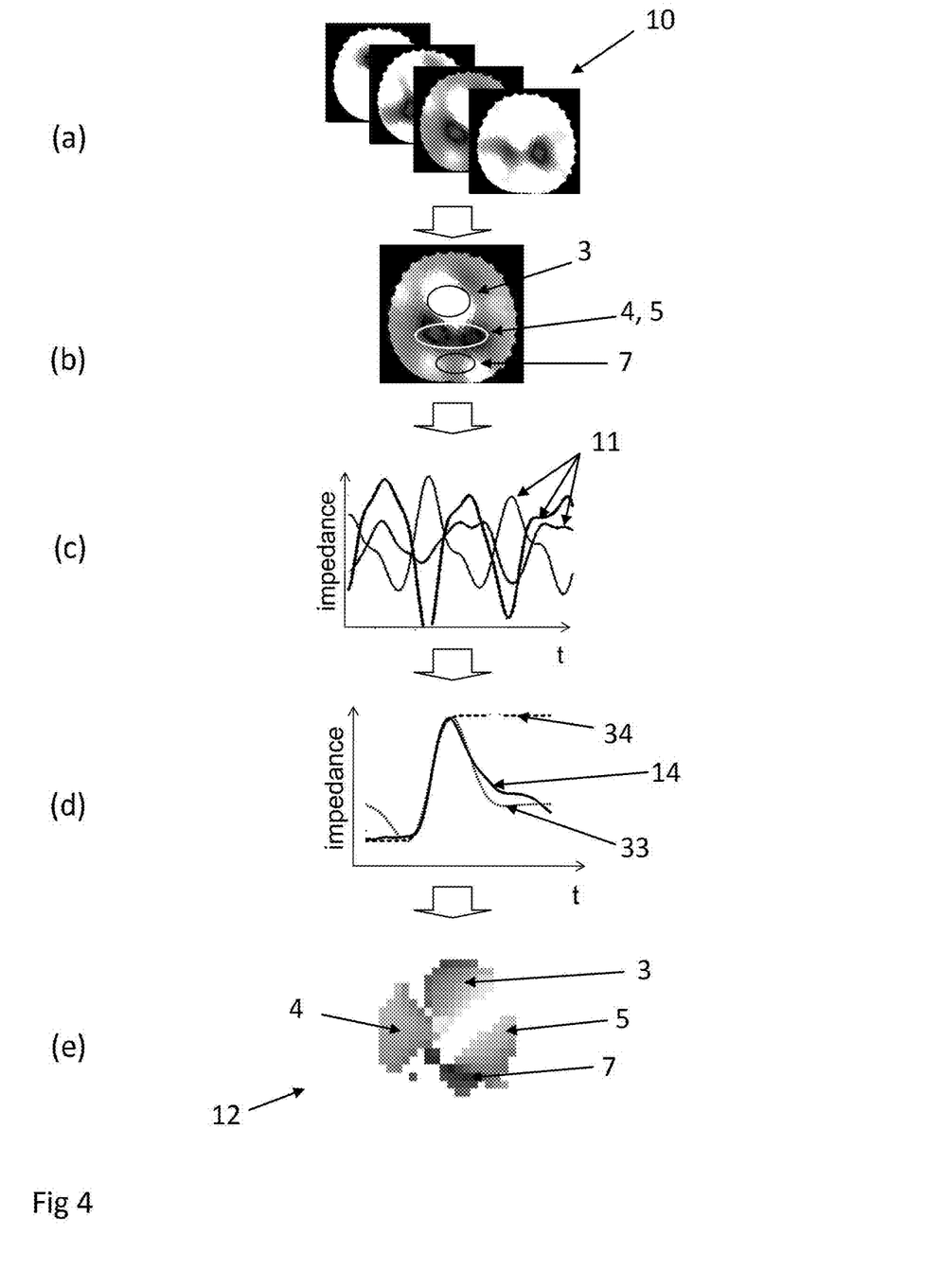
Figure 8:
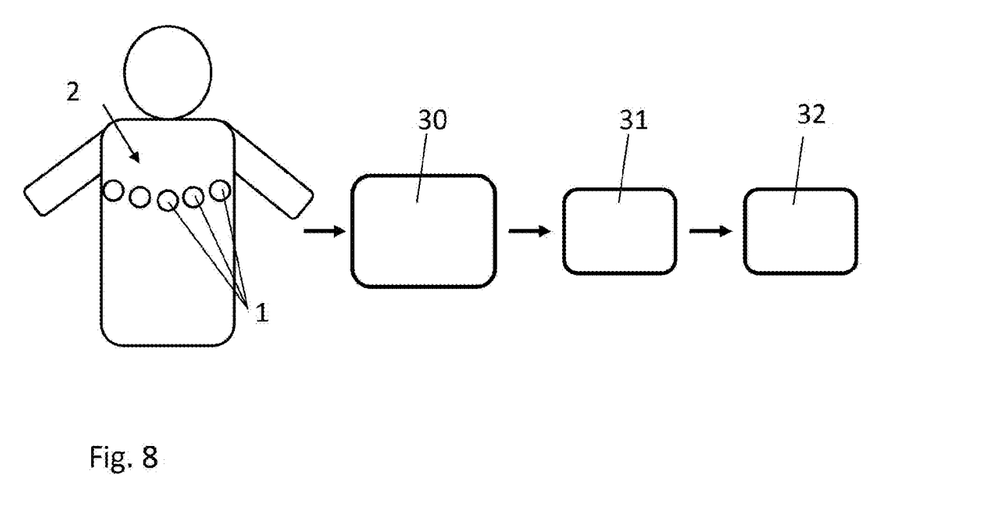
FIG. 8 schematically shows an apparatus for estimating PAT values in the measurement region of the subject, according to an embodiment.

In an embodiment, the method for estimating PAT values in a measurement region of the subject, comprises (see FIGS. 4 (a) to (d)):

providing an EIT imaging device (see FIG. 8) adapted to record impedance signal distribution (EIT image) within a measurement region of the subject;

measuring a sequence of temporally discrete EIT images 10 during a predetermined measuring time period in the measurement region using the EIT imaging device, each EIT image comprising one or a plurality of EIT pixel subsets, each of said one or a plurality of EIT pixel subset representing an impedance value;

generating one or a plurality of time series 11, each of said one or a plurality of time series 11 representing a variation of the impedance value of the sequence of EIT images 10; and estimating the PAT value from each of said one or a plurality of time series 11.

Said generating a time series can be performed for each pixel of the EIT image, i.e., each of said one or a plurality of EIT pixel subsets comprises one pixel representing the impedance value. Alternatively, said generating a time series can be performed for a group of a plurality of pixels, i.e., each of said one or a plurality of EIT pixel subsets comprises a plurality of pixels, the plurality of pixels representing the impedance value. Preferably, each of the EIT pixel subset is located in a region of interest (ROI). Preferably, the ROI corresponds to the left- and/or right-ventricular contraction of the subject. The ROI can also correspond to descending aorta. Preferably, said predetermined measuring time period comprises at least a complete cardiac cycle.

In an embodiment, the method further comprises generating a time-based PAT image representative of the sequence of EIT images, the time-based PAT image comprising one or a plurality of PAT-based pixel subsets wherein each of the one or a plurality of PAT pixel subsets corresponds to one estimated PAT value.

Said estimating a PAT value can comprise an analysis of the time series. Analysis examples comprises (see FIGS. 4 (a) to (e)):

the PAT value can be estimated as the time t1 corresponding to a characteristic point 13 of the time series 11, as described in Reference 7: "Parametric estimation of pulse arrival time: a robust approach to pulse wave velocity", J. Solà, et al., Physiol. Meas., 2009, Vol. 30; and the PAT value can be estimated as the time t1 corresponding to a parameter of a model of the pressure pulse 14 as described in Reference 7.

FIGS. 4 (a) to (e) illustrate the different steps of the method in the construction of the time-based EIT image, comprising the generation of a time-based image from a sequence of EIT images 10. For each pixel in the original sequence, a single PAT value is estimated depicting the time at which a pressure reaches the associated region within the thorax. More particularly, FIG. 4 (a) shows a sequence of EIT images 10; and FIG. 4 (b) shows the generating, for each pixel in the sequence, of a time series 11 describing its impedance changes throughout the cardiac cycle. The regions corresponding to the heart 3, the right lung 4, left lung 5 and aorta 7 are shown In FIG. 4 (c), showing the variation of impedance in time (t), impedance pulses at the time series 11 are surrogates of pressure pulses, and maintain the same timing characteristics. FIG. 4 (d) shows that, for each EIT pixel, a PAT value is estimated by analyzing its associated impedance pulse 14; and in FIG. 4 (e) a PAT-based image 12 is generated, containing timing information for each EIT pixel in the sequence of EIT images 10. In the PAT-based image 12 of FIG. 4 (e), regions corresponding to the heart 3, the right lung 4, left lung 5, and aorta 7 are visible. In FIG. 4 (d), the impedance pulse waveform 14 can be provided from each of said one or a plurality of time series. For example, an ensemble-averaged impedance pulse waveform corresponds to each of said one or a plurality of time series averaged over the predetermined measuring time period corresponding to a cardiac cycle.

An alternative method consists on performing ECG-gated ensemble averaging of the time series. A PAT value is then estimated from the averaged impedance pulse waveform 14. In another embodiment, the EIT imaging device further comprises an ECG device (not shown) for measuring an ECG signal during the predetermined measuring time period, allowing the ECG-gated ensemble averaging of the impedance time series 11. More particularly, the R wave of the measured ECG signal can be used for triggering the onset of the cardiac cycle and synchronizing different cardiac cycles as represented by the impedance time series 11. Synchronized cardiac cycles can then be averaged to obtain a single representative ECG-gated ensemble averaged impedance pulse waveform 14 for each time series 11. Said estimating a PAT value can be performed from the ECG-gated ensemble averaged impedance pulse waveform 14 of the time series 11.

An alternative method consists on performing left- and/or right-ventricular gated ensemble averaging of the time series 11. Left- and/or right-ventricular contraction gating is to be obtained from the same sequence of EIT images 10. A PAT value is then estimated from the averaged impedance pulse waveform 14. In other words, each of the one or a plurality of the time series 11 is ensemble averaged using EIT-gated ensemble averaging procedure. The EIT-gated ensemble averaging procedure can comprise using the onset of left- and/or right ventricular contraction detected from the sequence of EIT images 10. This can be achieved by using the impedance signal from the EIT pixel subset comprised in the left- and/or right-ventricular ROIs 4, 5. Such left- and/or right-ventricular contraction gating can be obtained from the sequence of EIT images 10. Said estimating a PAT value can be performed from the ensemble averaged impedance pulse waveform 14 of the time series 11.

The estimation of PAT values for each time series 11 can be performed via state-of-the-art techniques as described in Reference 7. In particular, parametric estimation of PAT is recommended since it provides not only PAT values, but also confidence indexes for the fitted model. An alternative method consists then of constructing time-based images taking in account only those PAT values whose confidence index exceeds a certain threshold. Other selection criteria might be included as well.

Figure 3:
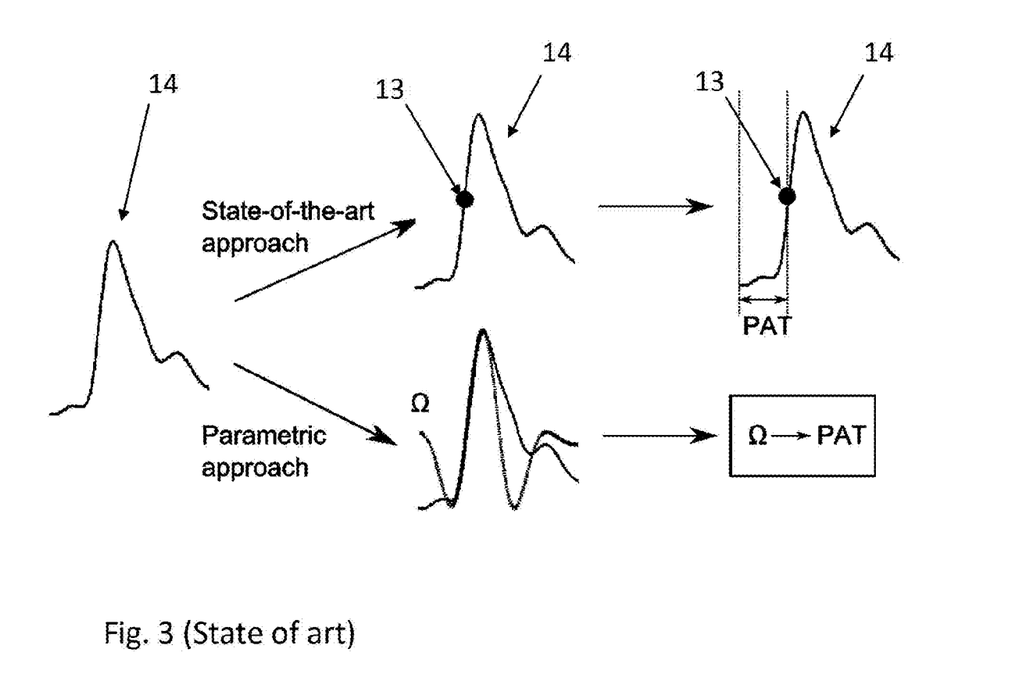
FIG. 3 illustrates estimating pulse arrival time (PAT) value using single-point and parametric-based method.

Accordingly in Reference 7, the parametric modeling of pressure pulse waveforms provide a single PAT value for each pressure tracing. While direct pressure tracings are obtained by means of an arterial line, examples of surrogate measurements are: photo-plethysmographic recordings, ultra-sound recordings and pixel-based MRI recordings. An example of parametric estimation of PAT is provided in FIG. 3. More particularly, FIG. 3 shows state-of-the-art estimation of PAT consisting in detecting a characteristic point 13 within the pressure pulse waveform 14. Parametric estimation of PAT consists of first fitting a parametric model to the original pressure pulse waveform, and then processing the parameters of the model in order to obtain PAT equivalent values.

In an embodiment, estimating the PAT value comprises fitting a parametric model to the time series 11 and processing parameters of the parametric model in order to obtain PAT equivalent values, such as described in Reference 7. The PAT value can also be estimated by fitting a parametric model to said impedance pulse waveform 14, for example, using Equation 1:

$$PAT = \Psi argmin_{\Omega} E[(p(t) - m_{\Omega}(t))^2]$$  Equation (1)

where $m_{\Omega}(t)$ is the parametric model of the pressure pulse waveform (time series) determined by the set of parameters $\Omega$, $E[\cdot]$ depicts mathematical expectation over one pressure pulse and $\Psi$ is a transformation from the parameters space to the time domain, i.e., $\Psi:\Omega \rightarrow t$. The PAT value of a given pulse waveform p(t) is estimated by first finding the parametric model $m_{\Omega}(t)$ that best fits to p(t), and by then transforming the parametric description $m_{\Omega}(t)$ into time domain values of PAT (see FIG. 3). As described in Reference 7, the parametric model $m_{\Omega}(t)$ can be defined according to a Morlet wavelet design (MOR), indicated by curve 33 in FIG. 4 (d), or according to a hyperbolic tangent function (THAN), indicated by curve 34 in FIG. 4 (d).

In another embodiment, estimating the PAT value comprises applying a single-point-based technique, as described in Reference 7. Accordingly, a PAT value can be obtained as the time t1 corresponding to the characteristic point 13 of the time series 11. Possible characteristic points 13 are the maximum of the time series 11, the foot of the time series 11, the maximum of the time series first derivative, or the maximum of the time series second derivative.

In yet another embodiment, generating the time-based PAT image comprises a step of discarding PAT values according to a selection criterion. The selection criteria can be a confidence index obtained when estimating the PAT value from the time series 11. Particularly, confidence indexes can be obtained from the estimation of PAT values by means of the parametric modeling approach. A confidence index can be the residual error of the minimization operator depicted by Equation 1. Additionally, a confidence index can be derived from the combination of any of the estimated parameters $\Omega$.

EXAMPLES

Figure 5:
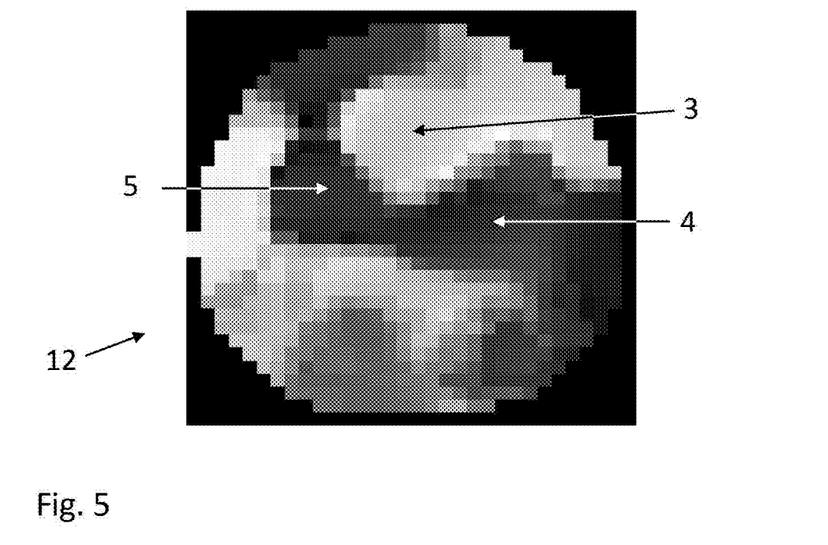
FIG. 5 depicts a time-based PAT image, according to an embodiment.

FIG. 5 illustrates a PAT-based image 12 obtained from a 1 minute recording for a ventilated pig. PAT values were computed from 1024 ensemble averaged EIT images 10. The ensemble averaging procedure was gated by the onset of left-ventricular contraction, as estimated from the same sequence of images 10. Parametric estimation of PAT as described in Reference 7 was performed, according to the TANH method. Dark pixels depict PAT-based pixels with an early arrival of the pressure pulse. Bright pixels (visible in white in FIG. 5) depict PAT-based pixels with a later arrival of the pressure pulse. Note that while the pressure pulse propagation starts at the heart region 3 (estimated early pulse arrival time), later on it propagates to the lung regions 4, 5 (estimated late pulse arrival time).

FIG. 5 depicts PAT values of the time-based PAT image 12 for all EIT pixel subsets in the sequence of EIT images 10, independently of the confidence index provided by the PAT parametric estimation algorithm, i.e., provided when fitting the parametric model to the time series. For some EIT pixel subsets, the obtained PAT value is not reliable enough because it either corresponds to a transition EIT pixel subset (for instance a pixel containing both cardiac and pulmonary information), or it depicts an anatomical region being poorly perfused. Thus, the confidence index needs to be included to discard non-reliable and meaningless estimations.

Figure 6:
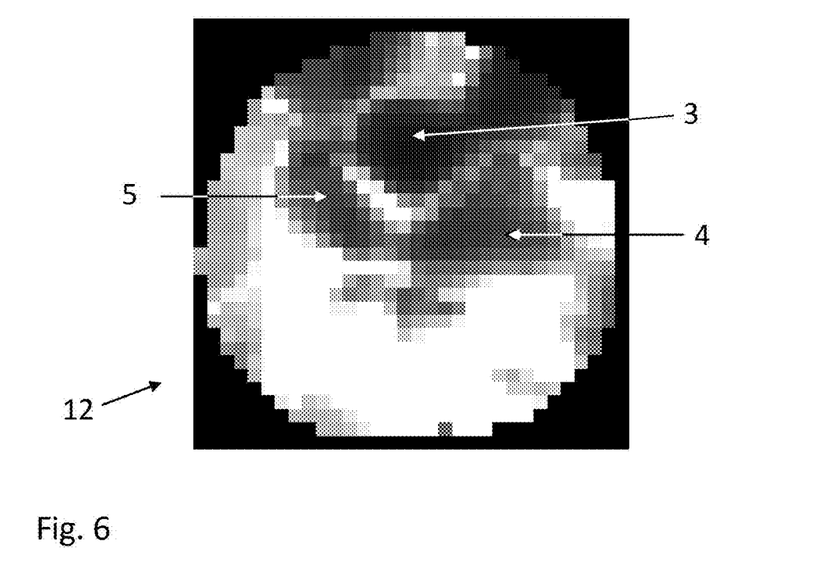
FIG. 6 illustrates a time-based PAT image comprising confidence index associated, according to an embodiment.
Figure 7:
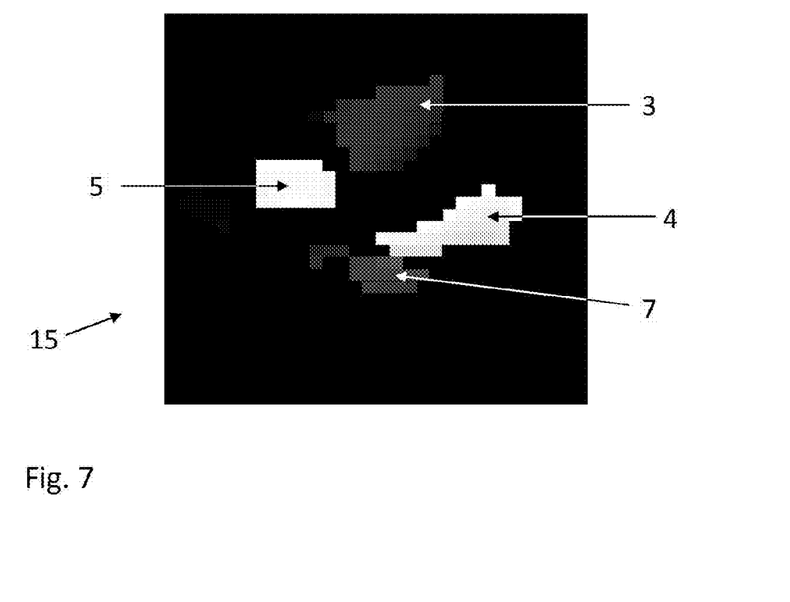
FIG. 7 illustrates a time-based PAT image, according to another embodiment.

FIG. 6 illustrates the PAT confidence index associated with each PAT-based pixel (PAT pixel subset), as estimated by the PAT estimation algorithm, i.e., when estimating the PAT value from the time series. In FIG. 6, dark pixels depict reliable PAT estimations and bright pixels (visible in white in FIG. 6) depict non-reliable PAT estimations. Discarding the pixels for which the PAT estimation was not reliable enough, and those for which the amplitude of the impedance pulse was too small, yields the time-based image 15 shown in FIG. 7. Each PAT-based pixel in the generated time-based image 15 of FIG. 7 depicts the delay, or PAT value, (in ms) from the onset of left- and/or right ventricular contraction, to the arrival time of the pressure pulse at the anatomical structures associated with the pixel.

The method for detecting PAT values disclosed herein not only provides new insights into the interpretation of sequences of EIT images depicting information on pulse propagation velocities and pathways, but it highlights small anatomical structures such as the aorta that were impossible to visualize using the state-of-the-art energy-based imaging. Moreover, the method allows for providing absolute physiological quantities expressed in measurement units of current use in clinical practice, and for detecting and monitoring organs and anatomical structures represented by small regions of interest such as the aorta or the pulmonary arteries.

The method further allows for providing the above information in an automatic and unsupervised way. This can be done without having to rely on a-priori information about the thoracic structure to be analyzed, overcoming the drawbacks of energy-based processing of conventional methods.

The present disclosure also pertains to an apparatus (see FIG. 8) for estimating PAT values in the measurement region of the subject using the method disclosed herein. In an embodiment, the apparatus comprises an EIT imaging device comprising a plurality of electrodes 1 to be placed in operative cooperation with the chest 2 of the subject and adapted to measure the sequence of temporally discrete EIT images 10; an input module 30 for inputting the sequence of EIT images 10, a processing unit 31 for performing the step of estimating the PAT value; and an output module 32 for outputting the PAT value. The processing unit 31 can be further adapted for generating the time-based PAT image 12. The output module 32 can also be arranged displaying and/or post-processing the time-based PAT images 12.

Reference Numbers 1 electrodes
2 chest
3 heart
4 right lung
5 left lung
6 back bone
7 aorta
10 sequence of electrical impedance tomography images
11 time series
12 PAT-based image
13 characteristic point
14 pressure pulse waveform
15 time-based image
30 input module
31 processing unit
32 output module
33 Morlet wavelet design parametric model
34 hyperbolic tangent function parametric model

The invention claimed is:

1. Method for estimating an arrival time value of arterial pressure pulses (PAT value) of a subject from a sequence of electrical impedance tomography (EIT) images, comprising:
   providing an EIT imaging device adapted to record impedance signal distribution (EIT image) within a measurement region of the subject;
   measuring a sequence of temporally discrete EIT images during a predetermined measuring time period in the measurement region using the EIT imaging device, each EIT image comprising one or a plurality of EIT pixel subsets, each of said one or a plurality of EIT pixel subset representing an impedance value;
   generating one or a plurality of time series, each of said one or a plurality of time series representing a variation of the impedance value of the sequence of one or plurality of EIT pixel subsets;
   estimating the PAT value from each of said one or a plurality of time series; and
   reporting the estimated PAT value.

2. Method according to claim 1, further comprising:
   generating a time-based PAT image representative of the sequence of EIT images, said time-based PAT image comprising one or a plurality of PAT pixel subsets, each said one or a plurality of PAT pixel subsets corresponding to the estimated PAT value.

3. Method according to claim 2, further comprising discarding PAT values according to a selection criterion.

4. Method according to claim 3, wherein said selection criterion is a confidence index obtained when estimating the PAT value.

5. Method according to claim 1, wherein each of said one or a plurality of EIT pixel subsets comprises one pixel representing the impedance value.

6. Method according to claim 1, wherein each of said one or a plurality of EIT pixel subsets comprises a plurality of pixels, said plurality of pixels representing the impedance value.

7. Method according to claim 6, wherein at least one EIT pixel subset is located in a region of interest (ROI).

8. Method according to claim 7, wherein said ROI corresponds to the left- and/or right-ventricular contraction of the subject.

9. Method according to claim 1, wherein said estimating the PAT value comprises detecting a characteristic point in each of said one or a plurality of time series.

10. Method according to claim 1, wherein said estimating the PAT value comprises fitting a parametric model to each of said one or a plurality of time series.

11. Method according to claim 1, further comprising providing an ensemble-averaged impedance pulse waveform from each of said one or a plurality of time series.

12. Method according to claim 11, wherein said providing an ensemble-averaged impedance pulse waveform comprises ensemble averaging each of said one or a plurality of time series using an ECG-gated ensemble averaging procedure.

13. Method according to claim 11, wherein said providing an ensemble-averaged impedance pulse waveform comprises ensemble averaging each of said one or a plurality of time series using an EIT-gated ensemble averaging procedure.

14. Method according to claim 13, wherein said EIT-gated ensemble averaging procedure comprises using the onset of left- and/or right ventricular contraction detected from the sequence of EIT images.

15. Method according to claim 11, wherein said estimating the PAT value comprises detecting a characteristic point in said impedance pulse waveform.

16. Method according to claim 11, wherein said estimating the PAT value comprises fitting a parametric model to said impedance pulse waveform.

17. Method according to claim 16, wherein said parametric model comprises a Morlet wavelet design or a hyperbolic tangent function.

18. Apparatus for estimating an arrival time value of arterial pressure pulses (PAT value) of a subject from a sequence of electrical impedance tomography (EIT) images, the apparatus comprising:
   an EIT imaging device comprising a plurality of electrodes to be placed in operative cooperation with the chest of the subject and adapted to record impedance signal distribution (EIT image) within a measurement region of the subject and adapted to measure the sequence of temporally discrete EIT images during a predetermined measuring time period in the measurement region, each EIT image comprising one or a plurality of EIT pixel subsets, each of said one or a plurality of EIT pixel subset representing an impedance value;
   an input module for inputting the sequence of EIT images;
   a processing unit for generating one or a plurality of time series, each of said one or a plurality of time series representing a variation of the impedance value of the sequence of EIT images of one or a plurality of EIT pixel subsets estimating the PAT value from each of said one or a plurality of time series; and
   an output module for outputting the estimated PAT value.

19. Method for estimating an arrival time value of arterial pressure pulses (PAT value) of a subject from a sequence of electrical impedance tomography (EIT) images, comprising:

providing an EIT imaging device adapted to record impedance signal distribution (EIT image) within a measurement region of the subject;

measuring a sequence of temporally discrete EIT images during a predetermined measuring time period in the measurement region using the EIT imaging device, each EIT image comprising one or a plurality of EIT pixel subsets, each of said one or a plurality of EIT pixel subset representing an impedance value;

generating one or a plurality of time series, each of said one or a plurality of time series representing a variation of the impedance value of the sequence of one or plurality of EIT pixel subsets; and estimating the PAT value from each of said one or a plurality of time series;

reporting the estimated PAT value; and generating a time-based PAT image representative of the sequence of EIT images, said time-based PAT image comprising one or a plurality of PAT pixel subsets, each said one or a plurality of PAT pixel subsets corresponding to the estimated PAT value.

20. Method for estimating an arrival time value of arterial pressure pulses (PAT value) of a subject from a sequence of electrical impedance tomography (EIT) images, comprising:

providing an EIT imaging device adapted to record impedance signal distribution (EIT image) within a measurement region of the subject;

measuring a sequence of temporally discrete EIT images during a predetermined measuring time period in the measurement region using the EIT imaging device, each EIT image comprising one or a plurality of EIT pixel subsets, each of said one or a plurality of EIT pixel subset representing an impedance value;

generating one or a plurality of time series, each of said one or a plurality of time series representing a variation of the impedance value of the sequence of one or plurality of EIT pixel subsets; and estimating the PAT value from each of said one or a plurality of time series;

reporting the estimated PAT value; and providing an ensemble-averaged impedance pulse waveform from each of said one or a plurality of time series.

* * * * *